(12) United States Patent
Ducauchuis

(10) Patent No.: US 7,727,611 B2
(45) Date of Patent: Jun. 1, 2010

(54) FILM COMPRISING INDIVIDUAL ANCHORED FILAMENTS

(75) Inventor: Jean-Pierre Ducauchuis, Nantes (FR)

(73) Assignee: APLIX, Paris (FR)

( * ) Notice: Subject to any disclaimer, the term of this patent is extended or adjusted under 35 U.S.C. 154(b) by 617 days.

(21) Appl. No.: 11/587,829

(22) PCT Filed: May 20, 2005

(86) PCT No.: PCT/FR2005/001269

§ 371 (c)(1),
(2), (4) Date: Oct. 25, 2006

(87) PCT Pub. No.: WO2005/122816

PCT Pub. Date: Dec. 29, 2005

(65) Prior Publication Data

US 2007/0233023 A1    Oct. 4, 2007

(30) Foreign Application Priority Data

May 21, 2004   (FR)    ................................. 04 05513

(51) Int. Cl.
| | |
|---|---|
| B32B 3/02 | (2006.01) |
| B32B 3/14 | (2006.01) |
| B32B 3/16 | (2006.01) |
| B27N 3/04 | (2006.01) |
| B29C 65/00 | (2006.01) |
| A61F 13/15 | (2006.01) |
| A44B 18/00 | (2006.01) |

(52) U.S. Cl. .............................. 428/92; 428/96; 428/99; 24/448; 24/447; 24/442; 264/241; 264/243; 264/248; 264/249; 264/257

(58) Field of Classification Search ................... 428/85, 428/92, 96, 99, 100, 114; 24/442, 447, 448; 442/366; 264/239, 241, 243, 248, 249, 257; 604/358

See application file for complete search history.

(56) References Cited

U.S. PATENT DOCUMENTS 4,994,054 A    2/1991   Pigneul et al. ............... 604/391

(Continued)

FOREIGN PATENT DOCUMENTS

EP    0 289 198    11/1988

(Continued)

OTHER PUBLICATIONS

International Search Report issued in PCT/FR2005/001269 on Oct. 28, 2005, 2 pages.

*Primary Examiner*—Cheryl Juska
(74) *Attorney, Agent, or Firm*—Renner, Kenner, Greive, Bobak, Taylor & Weber

(57) ABSTRACT

The invention relates to a film comprising individual anchored filaments. More specifically, the invention relates to the female part of a hook-and-loop self-adhering support, comprising a plastic film and independent filaments which are fixed to one of the faces of the film. The invention is characterized in that part of the length of each filament is anchored to the plastic film, while the remainder thereof is disposed at a distance from the film, such as to form loops. According to the invention, the film is made from a non-elastic and non-heat-shrinkable material and the filaments have a count of less than 10, preferably less than or equal to 7.7, for example between 2 and 5 decitex.

11 Claims, 3 Drawing Sheets

U.S. PATENT DOCUMENTS

| | | | |
|---|---|---|---|
| 6,319,593 B1 * | 11/2001 | Kenmochi et al. | 428/198 |
| 6,506,472 B1 * | 1/2003 | Tanaka et al. | 428/105 |
| 6,774,070 B1 * | 8/2004 | Kenmochi et al. | 442/352 |
| 6,888,045 B2 * | 5/2005 | Wahlstrom et al. | 604/378 |
| 6,955,668 B2 * | 10/2005 | Almberg et al. | 604/392 |
| 7,003,856 B2 * | 2/2006 | Hayashi et al. | 28/282 |
| 7,228,587 B2 * | 6/2007 | Tanaka et al. | 15/229.3 |
| 7,334,287 B2 * | 2/2008 | Tanaka et al. | 15/229.3 |
| 2002/0026699 A1 * | 3/2002 | Hayashi et al. | 28/282 |
| 2002/0168497 A1 * | 11/2002 | Lester et al. | 428/100 |
| 2003/0069558 A1 * | 4/2003 | Almberg et al. | 604/392 |
| 2005/0003143 A1 * | 1/2005 | Ducauchuis et al. | 428/92 |
| 2007/0233023 A1 * | 10/2007 | Ducauchuis | 604/358 |

FOREIGN PATENT DOCUMENTS

| | | |
|---|---|---|
| WO | WO 97/25893 | 7/1997 |
| WO | WO 01/33989 | 5/2001 |

* cited by examiner

FILM COMPRISING INDIVIDUAL ANCHORED FILAMENTS

TECHNICAL FIELD

The present invention relates to a female loop section for a self-gripping hook and loop fastening, intended in particular for use for fastening training pants. The present invention also relates to a method of producing a female loop section of this type.

BACKGROUND ART

Numerous devices and methods are described in patents relating to these female loop sections for hook and loop fastenings and in particular in the field of training pants. Taking into account the production imperatives, it is desirable to make available a female loop section which is as cost-effective as possible and to be able to produce it with the quickest production rate possible. For example the European patent No. 0 289 198 in the name of Procter & Gamble Company discloses a female loop section constituted by a film made of an elastic material and filaments soldered to the film according to a soldering pattern, the soldering being realised in such a way that loops are formed by the filaments between themselves and the film. In order to do this, it is necessary to provide a film made of an elastic material, even thermo-retractable. The production method of these female sections is complicated to implement, particularly by reason of the fact that a soldering stage and a film retraction stage are provided for forming the loops. Thus, the female section obtained is particularly costly. In fact, an elastic material (we are not even talking about a thermo-retractable material) is a costly material on the one hand and on the other hand the filaments, in order to withstand the different operations (soldering and stretching), are filaments with large diameters, particularly greater than 10 decitex, thus resulting in a high cost.

DISCLOSURE OF THE INVENTION

The present invention relates to a method of producing a female section of a fastening which allows a female fastening section to be obtained at a very low cost on the one hand and which allows production thereof at a high rate on the other hand. Besides, the use of thin filaments also allows a very soft handle because the filament, being extruded, is in a material state of weak orientation which allows great suppleness and softness. Good readability of the designs which may be printed below the film is also obtained.

According to the invention the method of production of a female fastening section, comprising a film made of plastic material and filaments fixed on one of the faces of the film in order to form loops, is characterised in that it comprises the stages which consist in:
  shaping, by extrusion, a film made of plastic material;
  passing a filament curtain between a belt or a pressing roller and a shaping roller in such a way as to provide each filament with a form with hollows and bosses;
  bringing the filaments in the form of hollows and bosses into contact with the softened plastic material of the film, after extrusion, on the surface thereof, through application of an electrostatic field in order to anchor, through electrostatic pressure, the filaments in the material of the softened plastic film, in such a way that the boss sections of the filaments form the loops whereas the hollow sections are anchored in the plastic material.

The production method is thus particularly rapid and allows large-scale production of female loop sections for fastenings, particularly in the field of training pants.

Preferably, according to a preferred embodiment, the filaments have a titre of less than 10 decitex and in particular less than 7.7 decitex, particularly between 2.2 and 5.5 decitex.

Preferably, the film made of plastic material has a thickness between 10 and 20 µm or 30 µm when it is to be printed and between 5 and 15 µm without printing.

According to a preferred embodiment of the invention the plastic material film comprises a non-elastic material at least in the direction of the filaments (running direction of the film) and is also non-thermo-retractable.

An elastic material is to be understood to be a material which substantially resumes its original shape without deformation (that is to say particularly when it returns to a shape having dimensions of less than 105% of its initial dimensions) when it undergoes elongation in any direction over more than 120% of its initial dimensions in any said direction at rest.

A material which is not thermo-retractable is understood to be a material which, when subjected to heat, does not retract by more than 10%, particularly when it is subjected to a temperature equal to or greater than 140° for at least 10 seconds.

The present invention also relates to a female loop section for a hook and loop fastening, particularly for training pants, obtained by the method according to the invention.

According to the invention the female section, constituted by a plastic material film and filaments, independent from each other and fixed on one of the faces of the film, is characterised in that each filament is anchored over a section of its length in the plastic material film, while on other sections it is at a distance from the film for forming the loops;
  the film being, at least in the longitudinal direction of the filaments, made of a non-elastic and non-thermo-retractable material, and the sections forming loops of the filaments are independent from each other.

In the present invention, filaments or loop sections of filaments which are independent from each other are understood to be filaments or loop sections of filaments which are not connected to their neighbours, for example forming a sheet. According to the present invention, the filaments are connected between themselves solely by the plastic material film and not directly between themselves, even though it may arise in the final product that certain filaments come into contact with others in the sections forming loops. However, there is no fixing in the region of this contact and the filaments can be spaced apart from each other, unlike when they are formed in a sheet.

According to an embodiment,
  the filaments have a titre of less than 10 decitex, preferably less than or equal to 7.7, particularly between 2.2 and 5.5 decitex.

According to a preferred embodiment of the invention, the loops project from the film, having their bases arranged in rows, the rows being spaced apart from each other by an inter-row distance at least equal to 0.05 mm, in particular greater than or equal to 0.15 mm.

According to a preferred embodiment, the filaments are arranged on the film in a single layer, that is to say each filament is alone on the top of the film without another filament on top.

Preferably, the film has a thickness between 10 and 20 or 30 µm when it is to be printed, and between 5 and 15 µm without printing.

According to an advantageous embodiment, the filaments are multilobed, in particular trilobed or quadrilobed, whereby the non-round cross-section in the form of a clover with several leaves means that less thread material is necessary for simultaneously enclosing the filaments in the film.

According to an advantageous embodiment, the filaments are crimped or textured, thus enhancing the hold of the hooks by reason of the local rippling on the outer surface of the filaments themselves. Each thus crimped or textured filament is more easily distinguished from its neighbours.

BRIEF DESCRIPTION OF DRAWINGS

Solely by way of illustration, an embodiment of a method according to the invention and of a loop section obtained by a method according to the invention will now be described by reference to the drawings, in which.

PREFERRED EMBODIMENT FOR CARRYING OUT THE INVENTION

Figure 1:
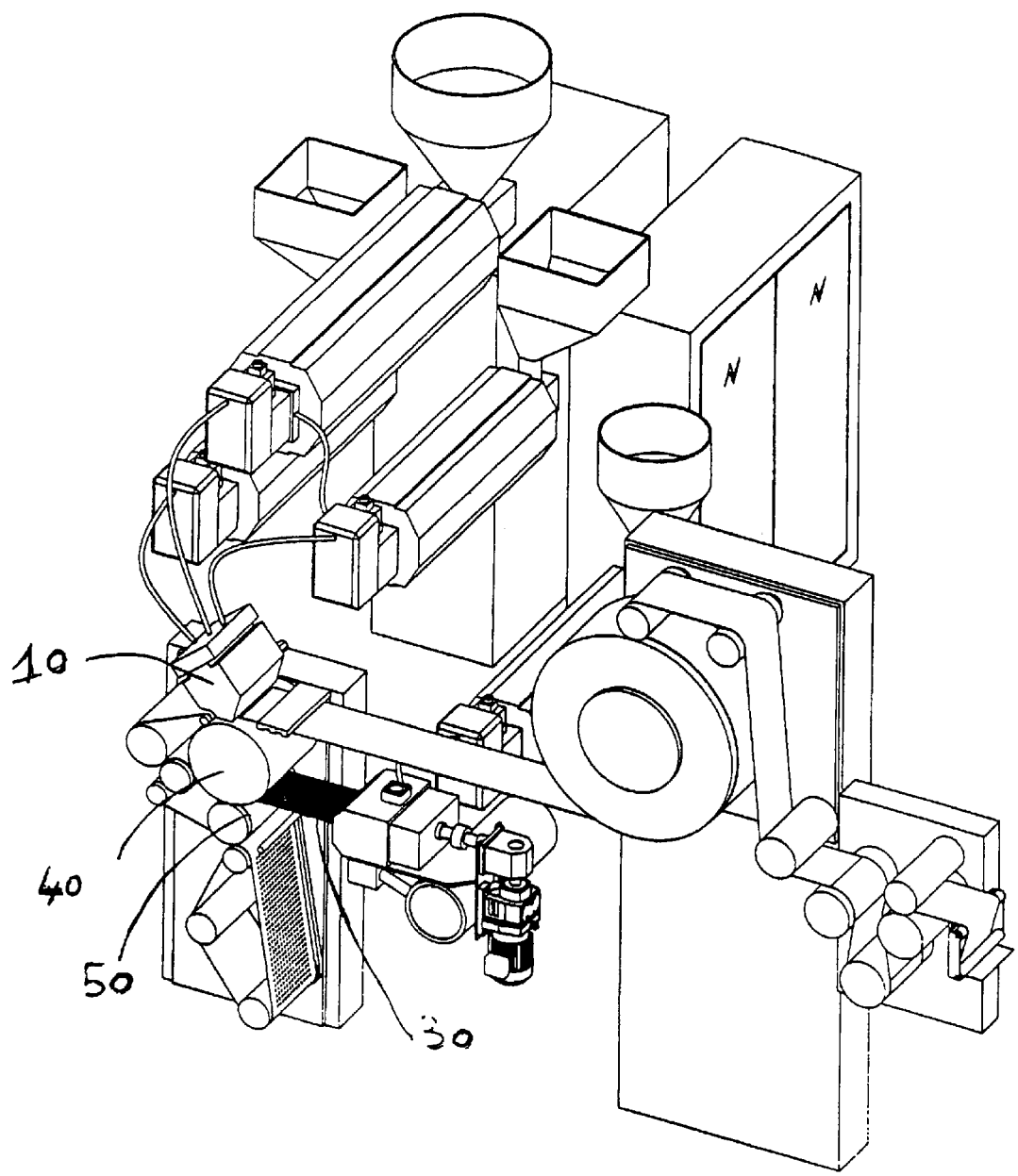
FIG. 1 is an overall view of a device for implementing the production method according to the invention.
Figure 2:
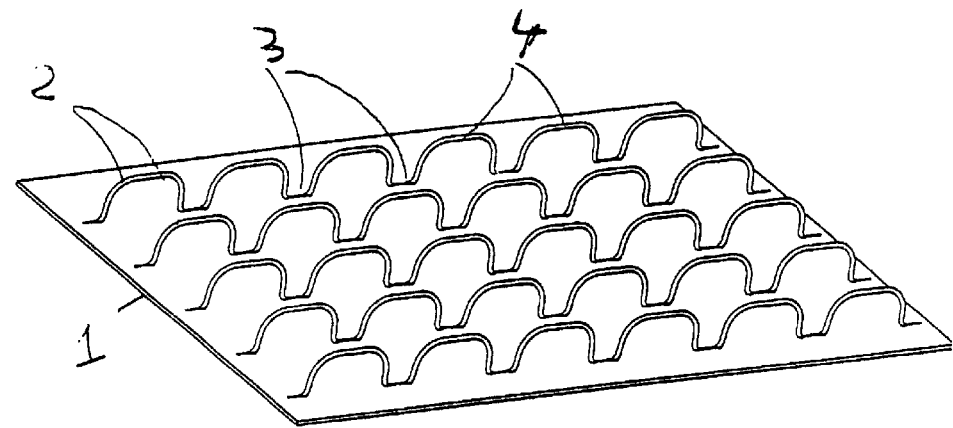
FIG. 2 is a perspective view of a loop section according to the invention.
Figure 3:
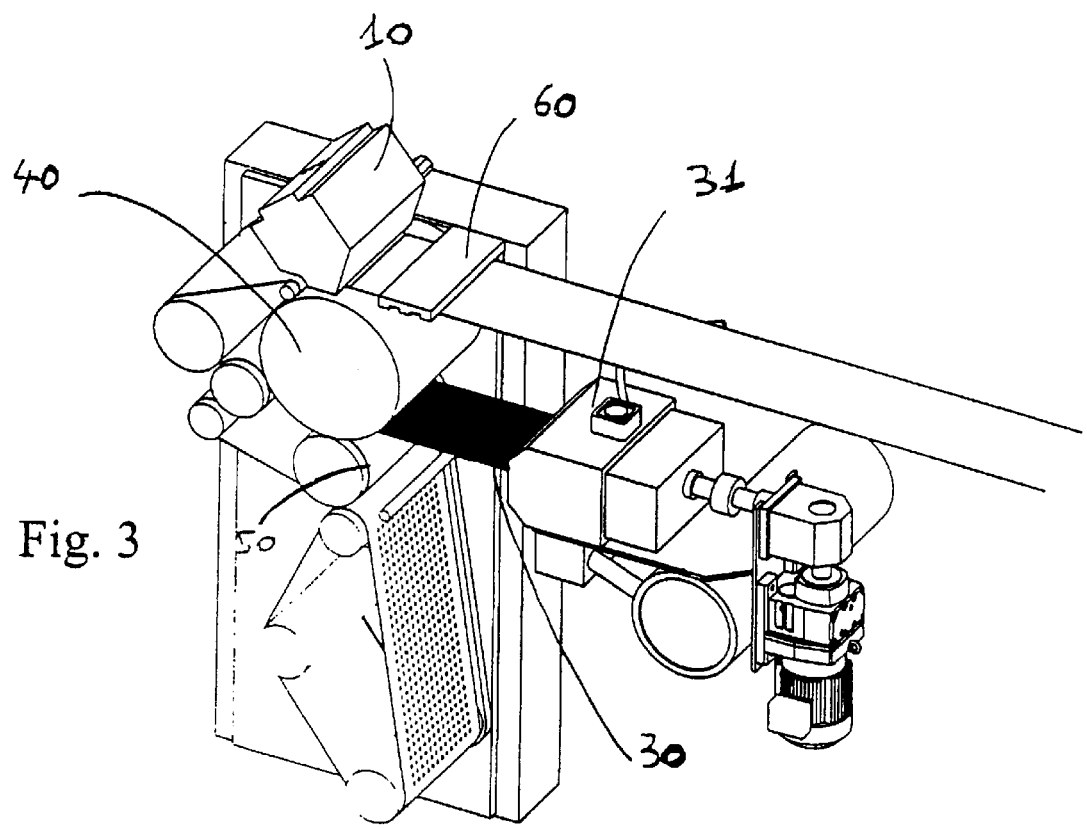
FIG. 3 shows a section of the device of FIG. 1 on a larger scale.
Figure 4A:
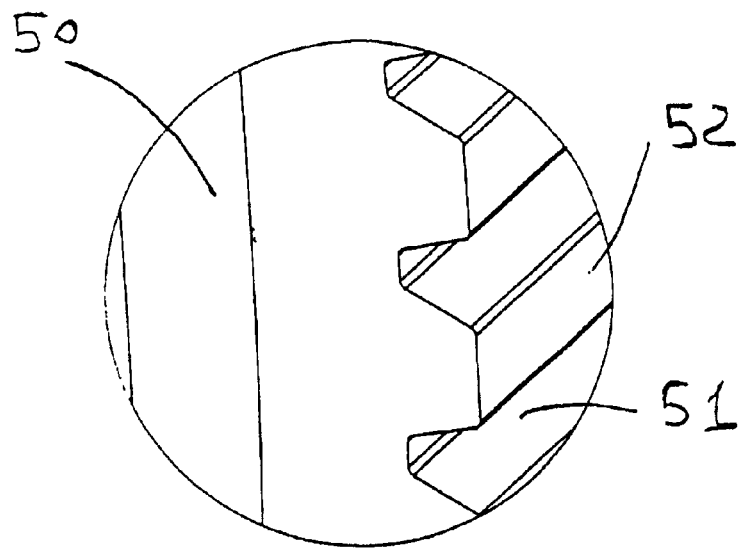
FIGS. 4a and 4b are views on a larger scale of sections of the shaping roller and the notched belt of the device of FIGS. 1 and 3.
Figure 4B:
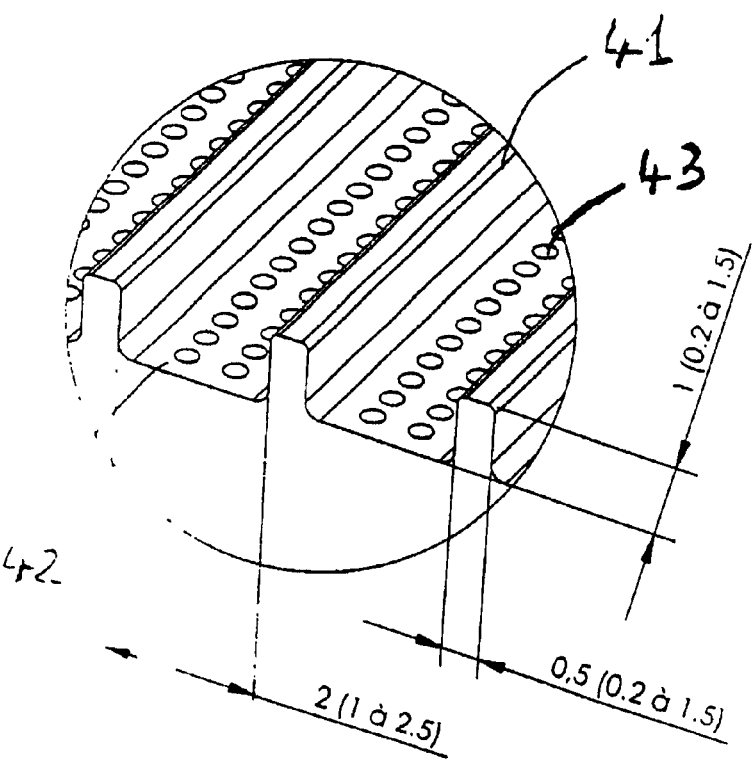

A loop section according to the invention can be seen in FIG. 2. This loop section is constituted by a film 1 made of non-elastic and non-thermo-retractable material, whereby filaments 2 are anchored in the film 1. The filaments 2 are arranged in rows on the film 1. Each filament 2 is constituted by a succession of hollow and boss sections, namely hollow sections or anchoring sections 3 and boss sections or sections forming loops 4. In the anchoring sections 3 the filaments are anchored in the plastic material of the film. In particular they are anchored partially in the plastic material of the film. The filaments have a titre equal to 5.5 decitex. Preferably, this title is strictly less than 10 decitex.

Each row of loops in the longitudinal direction in the drawing is spaced apart from the neighbouring rows by a distance equal to and preferably greater than 0.15 mm, particularly between 0.05 and 0.5 mm. This inter-row distance can vary from one row to another, particularly in order to avoid an alignment effect which is too pronounced.

In the drawing, the loops shown are well-aligned in a row. In fact, it generally arises that the loops are inclined to one side or the other and thus come into contact with a loop of a neighbouring row. Consequently, a more precise definition of a row consists in taking into account only the bases of loops which are always aligned, themselves, in rows.

The anchoring sections 3 extend over a length for example between 0.2 and 1.5 mm, for example 0.8 mm, the loops have a length between for example 0.5 mm and 2.5 mm, for example 1.6 mm, their height is approximately 1 mm, and may be between 0.2 mm and 1.5 mm for example.

The plastic material of the film which can be single-layer or multi-layer can be a polyolefine such as polypropylene or polyethylene (temperature on leaving the die being greater than the softening temperature generally between 120° C. and 180° C.), a polyamide or a polyester (temperature on leaving the die being greater than the softening temperature between 180° C. and 270° C.), or a modified copolymer (temperature on leaving the die being greater than the softening temperature between 80° C. and 180° C.) whereas the filaments can be for example polyamide, polyester or polypropylene.

The film can also be formed in multiple layers.

The production method of a loop section as shown in FIG. 2 is as follows:

Firstly, a softened plastic material film is extruded from an extrusion die 10 which is rotated at a speed equal to 300 m/mn, preferably between 200 and 500 m/mn.

On the other hand, a filament curtain 30 is extruded from a die 31 and is passed between a shaping roller 40 and a notched belt (or roller). The shaping roller 40 has slots in it. The notched belt 50 comprises grooves 51 of a shape complementary to the ribs 41 formed on the outer surface of the roller 40.

Likewise, between the grooves 51, blocks 52 are formed of a complementary form to hollowed-out areas 42 formed between the ribs 41.

At the bottom of the hollowed-out areas 42, suction orifices 43 are provided for plating, through suction, the filaments of the curtain 30 passing between the roller 40 and the belt 50. Thus, when the filament is pressed between the shaping roller 40 and the notched belt 50, it undergoes deformation such that it is gathered, being taken between the hollowed-out areas 42 and the complementary blocks 52. On leaving the shaping roller and the belt, the filaments have hollow and boss formations.

The filament curtain with hollows and bosses is thus brought into contact with the softened plastic material film directly following the extrusion of the plastic material film. An electrostatic device (electrostatic bar 60) of the Eltex type applies an electric field to the site of this contact of the filaments and the softened plastic material film. This electrostatic field which depends upon the travel speed and which can in particular be between 200 and 500 V/m allows the application of electrostatic pressure which anchors the hollow sections of the filaments in the plastic material film which is still softened, leaving the boss sections at a distance from the film, in such a way as to obtain a female section as shown in FIG. 2 on leaving the zone of the electrostatic field. Once the contact between the film and the filament has been realised following extrusion, the very rapid cooling of the plastic material brings about the anchoring of the filaments in the film.

In the case of a single-layer film, for example being made of polypropylene, the temperature of the film being applied to the filaments, for example also being of polypropylene, is in the range of 150° C. This temperature is greater than the softening temperature of polypropylene.

In the case of a multi-layer film, for example a first layer of polypropylene and a second layer of modified copolymer, the first layer is at a temperature of 150° C. and supports the second layer which is at a temperature which is greater than its fusion point (for example beyond 130° C.), the second layer serving as a connection layer with the filaments of a different material, for example made of polyamide, which facilitates the realisation of all the possible combinations for the materials of the film and the filaments.

This production method is particularly simple and rapid. The product obtained is particularly cost-effective since the film can be produced from a single plastic material which is neither elastic nor thermo-retractable and the filaments do not need to be of a great thickness and in particular the titres are strictly less than 10 decitex and preferably less than or equal to 7.7 decitex, particularly between 2.2 and 5.5 decitex. The female section obtained is thus particularly suitable for use in training pants where it is necessary to produce female sections in a large quantity and at the lowest cost possible.

The invention claimed is:

1. A female section of a hook and loop fastener, comprising a film made of a plastic material, said film being non-elastic at least in a longitudinal direction; and filaments, which are independent from each other and fixed to the film such that the filaments are connected between themselves solely by said film, each said filament having a titer which is greater than 2.2 decitex and less than 10 decitex, wherein each said filament includes alternatively anchored sections and loop forming sections, said anchored sections being straight lines extending along said longitudinal direction and being anchored in the plastic material of the film, while said loop forming sections are not fixed to the film so as to form loops, the bases of the loops being arranged in longitudinal rows which are spaced apart from each other by an inter-row distance which is greater than 0.05 mm.

2. The female section according to claim 1, characterised in that the filaments are arranged on the film in a single layer, so that each filament is alone on top of the film without another filament on top.

3. The female section according to claim 1, characterised in that the film has a thickness between 5 and 20 μm.

4. The female section according to claim 1, characterised in that the anchoring sections extend over a length between 0.2 and 1.5 mm, the loops have a length between 0.5 mm and 2.5 mm, their height being approximately 1 mm.

5. The female section according to claim 1, characterised in that the filaments are crimped or textured.

6. The female section according to claim 1, characterised in that the filaments are multilobed.

7. Training pants comprising a female section according to claim 1.

8. A method of producing a female fastening section according to claim 1, comprising the steps of:
   shaping, through extrusion, a plastic material film;
   passing a filament curtain between a belt or a pressing roller and a shaping roller in such a way as to give a hollow and boss formation to each filament;
   bringing the filaments in hollow and boss formation into contact with the softened plastic material of the film, following extrusion, on the surface thereof;
   application of an electrostatic field to anchor the filaments in the material of the film made of softened plastic material by electrostatic pressure in such a way that the boss sections of the filaments form loops whereas the hollow sections are anchored in the plastic material.

9. The method according to claim 8, characterised in that the filaments have a titre of less than 10 decitex.

10. The method according to claim 8, characterised in that the plastic material film comprises a non-elastic and non-thermo-retractable material.

11. The method according to claim 8, characterised in that a filament curtain is extruded from a die and is brought between a shaping roller and a belt or a notched roller, whereby the shaping roller has slots in it and the belt or notched roller comprise grooves of a complementary form to ribs formed on the outer surface of the roller, points of a complementary form to hollowed-out areas formed between the ribs being formed between the grooves at the bottom of the hollowed-out areas, suction orifices are provided which allow plating, through suction, of the filaments of the curtain passing between the roller and the belt.

* * * * *